United States Patent
Podhajsky et al.

(10) Patent No.: US 9,763,727 B2
(45) Date of Patent: *Sep. 19, 2017

(54) METHODS OF MANUFACTURING END EFFECTORS FOR ENERGY-BASED SURGICAL INSTRUMENTS

(71) Applicant: COVIDIEN LP, Mansfield, MA (US)

(72) Inventors: Ronald J. Podhajsky, Boulder, CO (US); William S. Darrow, Longmont, CO (US); Kristel L. Ambrosius, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 176 days.

This patent is subject to a terminal disclaimer.

(21) Appl. No.: 14/630,256

(22) Filed: Feb. 24, 2015

(65) Prior Publication Data

US 2015/0164577 A1 Jun. 18, 2015

Related U.S. Application Data

(63) Continuation of application No. 13/347,404, filed on Jan. 10, 2012, now Pat. No. 8,962,062.

(51) Int. Cl.
*A61B 18/14* (2006.01)
*A61B 18/00* (2006.01)

(52) U.S. Cl.
CPC ........... *A61B 18/14* (2013.01); *A61B 18/149* (2013.01); *A61B 18/1442* (2013.01); *A61B 2018/00107* (2013.01)

(58) Field of Classification Search
CPC .............................. A61B 5/0408; A61B 18/14

USPC ............................ 606/51; 600/391; 427/2.11
See application file for complete search history.

(56) References Cited

U.S. PATENT DOCUMENTS

| | | | |
|---|---|---|---|
| 3,908,263 A | 9/1975 | Matarese | |
| 4,393,584 A | 7/1983 | Bare et al. | |
| 5,057,106 A | 10/1991 | Kasevich et al. | |
| 5,352,315 A | 10/1994 | Carrier et al. | |
| 5,924,983 A | 7/1999 | Takaki et al. | |
| 5,925,040 A | 7/1999 | Nardella et al. | |
| 6,356,779 B1 | 3/2002 | Katzenmaier et al. | |
| 6,786,905 B2 | 9/2004 | Swanson et al. | |
| 6,929,644 B2 | 8/2005 | Truckai et al. | |
| 6,932,816 B2 | 8/2005 | Phan | |
| 7,041,102 B2 | 5/2006 | Truckai et al. | |
| 7,414,262 B2 * | 8/2008 | Anderson | H01L 29/66757 257/142 |
| 7,753,908 B2 | 7/2010 | Swanson | |
| 8,962,062 B2 * | 2/2015 | Podhajsky | A61B 18/1442 257/27 |

(Continued)

FOREIGN PATENT DOCUMENTS

| | | |
|---|---|---|
| EP | 1977707 A1 | 10/2008 |
| EP | 2357669 A2 | 8/2011 |

(Continued)

*Primary Examiner* — Dah-Wei D Yuan
*Assistant Examiner* — Andrew Bowman

(57) ABSTRACT

A method of manufacturing an end effector for a surgical instrument includes providing a substrate wherein at least an outer periphery of the substrate is formed from an electrically-insulative material. The method further includes forming at least one ridge on the outer periphery of the substrate and depositing an electrically-conductive material onto the at least one ridge to form at least one electrode.

16 Claims, 4 Drawing Sheets

(56) References Cited

U.S. PATENT DOCUMENTS

| | | |
|---|---|---|
| 2003/0130653 A1 | 7/2003 | Sixto et al. |
| 2003/0158549 A1 | 8/2003 | Swanson |
| 2003/0220637 A1 | 11/2003 | Truckai et al. |
| 2004/0260281 A1* | 12/2004 | Baxter, III ............. A61B 18/14 606/41 |
| 2007/0203489 A1 | 8/2007 | Suzuki |
| 2008/0262489 A1 | 10/2008 | Steinke |
| 2011/0082457 A1 | 4/2011 | Kerr et al. |

FOREIGN PATENT DOCUMENTS

| | | |
|---|---|---|
| EP | 2392272 A1 | 12/2011 |
| GB | 2292831 A | 3/1996 |
| WO | 96/33665 A1 | 10/1996 |
| WO | 2011/116303 A1 | 9/2011 |

* cited by examiner

METHODS OF MANUFACTURING END EFFECTORS FOR ENERGY-BASED SURGICAL INSTRUMENTS

CROSS-REFERENCE TO RELATED APPLICATIONS

This application is a continuation application of U.S. patent application Ser. No. 13/347,404, filed on Jan. 10, 2012, the entire contents of which are incorporated herein by reference.

BACKGROUND

Technical Field

The present disclosure relates to surgical instruments and, more particularly, to methods of manufacturing electrosurgical instruments capable of electrically treating tissue.

Background of Related Art

Various different processes are employed for depositing conductive film coatings, or inks, onto a substrate. Such processes include atomic layer chemical vapor deposition, combustion chemical vapor deposition, hot wire chemical vapor deposition, rapid thermal chemical vapor deposition, aerosol assisted chemical vapor deposition, direct liquid injection chemical vapor deposition, plasma-enhanced chemical vapor deposition, microwave plasma-assisted chemical vapor deposition, laser chemical vapor deposition, pressurized chemical vapor deposition, vapor phase epitaxy, cathodic arc deposition, electron beam physical vapor deposition, evaporative physical vapor deposition, pulsed laser physical vapor deposition, sputter physical vapor deposition, hybrid physical-chemical deposition, and other deposition processes.

More recently, additive manufacturing processes, such as direct-write deposition, have been developed for accurately depositing complex patterns and/or architectures of material onto a substrate. Direct-write deposition, for example, involves the use of a nozzle, or pen-like device that is controlled by computer aided design (CAD) software to deposit a specific pattern and/or architecture of material on the substrate.

Deposition processes, such as those mentioned above, are commonly used in semiconductor fabrication, although they also have applicability in a wide range of other fields. In particular, the ability to form electrode(s) by depositing conductive material onto an insulative substrate in complex patterns and architectures and/or on substrates having various different configurations has found application in energy-based surgical instrument manufacturing. However, electrosurgical electrodes having irregular edges formed during the deposition process may cause arcing upon application of energy thereto, which may ultimately damage surrounding tissue.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

In accordance with the present disclosure, a method of manufacturing an end effector for a surgical instrument is provided. The method includes providing a substrate wherein at least the outer periphery of the substrate is formed from an electrically-insulative material. The method further includes forming one or more ridges on the outer periphery of the substrate, and depositing an electrically-conductive material onto the one or more ridges to form one or more electrodes disposed on the outer periphery of the substrate.

In one aspect, the method further includes defining one or more reservoirs adjacent each ridge prior to depositing the electrically-conductive material onto the ridge.

In another aspect, the electrically-conductive material is deposited on the one or more ridges via one of direct-write deposition, chemical vapor deposition, and physical vapor deposition.

In yet another aspect, the substrate is formed wholly from an electrically-insulative material. Alternatively, the substrate may include an electrically-insulative coating defining the outer periphery thereof.

In still another aspect, one or more cut-outs are defined within the substrate to form the one or more ridges.

In another aspect, a plurality of ridges is formed on the outer periphery of the substrate. The ridges are configured such that a direct line-of-sight is established between electrodes of adjacent ridges.

In another aspect, the substrate forms a portion of, or the entire, end effector of an electrosurgical pencil, jaw member of an electrosurgical forceps, or other end effector or portion thereof of an energy-based surgical instrument.

The method may further include electrically connecting the one or more electrodes to a source of energy.

In still yet another aspect, the electrically-conductive material is gold, silver, or another suitable material.

Also provided in accordance with the present disclosure is another method of manufacturing an end effector for a surgical instrument. The method includes providing a substrate and forming one or more ridges on the outer periphery of the substrate. The method further includes forming a reservoir on the outer periphery of the substrate adjacent each side of the one or more ridges and depositing an electrically-conductive material onto the one or more ridges such that a portion of the electrically-conductive material overflows the ridge on either side thereof and is deposited in the reservoirs. The electrically-conductive material thus forms one or more electrodes disposed on the outer periphery of the substrate.

In one aspect, the electrically-conductive material is deposited on the one or more ridges via one of direct-write deposition, chemical vapor deposition, and physical vapor deposition.

In another aspect, a plurality of ridges is formed on the outer periphery of the substrate. The ridges are configured such that a direct line-of-sight is established between electrodes of adjacent ridges.

In yet another aspect, the substrate forms a portion of, or the entire, end effector of an electrosurgical pencil, jaw member of an electrosurgical forceps, or other end effector or portion thereof of an energy-based surgical instrument.

In still another aspect, the method further includes electrically connecting the one or more electrodes to a source of energy.

Another method of manufacturing an end effector for a surgical instrument provided in accordance with the present disclosure includes providing a substrate and defining one or more cut-outs within an outer periphery of the substrate to form one or more ridges on the outer periphery of the substrate. The method further includes depositing an electrically-conductive material onto the one or more ridges such that a portion of the electrically-conductive material overflows the ridge on either side thereof. The electrically-conductive material forms one or more electrodes disposed on the substrate.

In one aspect, the method further includes defining one or more reservoirs adjacent the one or more ridges prior to depositing the electrically-conductive material onto the one or more ridges.

In another aspect, the electrically-conductive material is deposited on the one or more ridges via one of direct-write deposition, chemical vapor deposition, and physical vapor deposition.

In still another aspect, the substrate forms a portion of, or the entire, end effector of an electrosurgical pencil, jaw member of an electrosurgical forceps, or other end effector or portion thereof of an energy-based surgical instrument.

In yet another aspect, a plurality of ridges is formed on the outer periphery of the substrate. The ridges are configured such that a direct line-of-sight is established between electrodes of adjacent ridges.

BRIEF DESCRIPTION OF THE DRAWINGS

Various embodiments of the present disclosure are described herein with reference to the drawings wherein like reference numerals identify similar or identical elements.

DETAILED DESCRIPTION

The operating features and inter-cooperating components of energy-based surgical instruments 100, 200 provided in accordance with the present disclosure are shown in the figures and are described hereinbelow. More specifically, although only an electrosurgical pencil 100 (FIGS. 1-2) and an electrosurgical forceps 200 (FIGS. 3-4) are shown, the present disclosure is equally applicable for use in conjunction with any energy-based surgical instrument having an end effector including one of more electrodes configured to conduct energy to tissue to electrically treat tissue. Obviously, different mechanical and electrical considerations apply to each particular type of instrument; however, the novel aspects with respect to the end effectors and the manufacture thereof remain generally consistent regardless of the particular type of instrument used. For the purposes herein, electrosurgical pencil 100 (FIGS. 1-2) and electrosurgical forceps 200 (FIGS. 3-4) are generally described.

Figure 1:
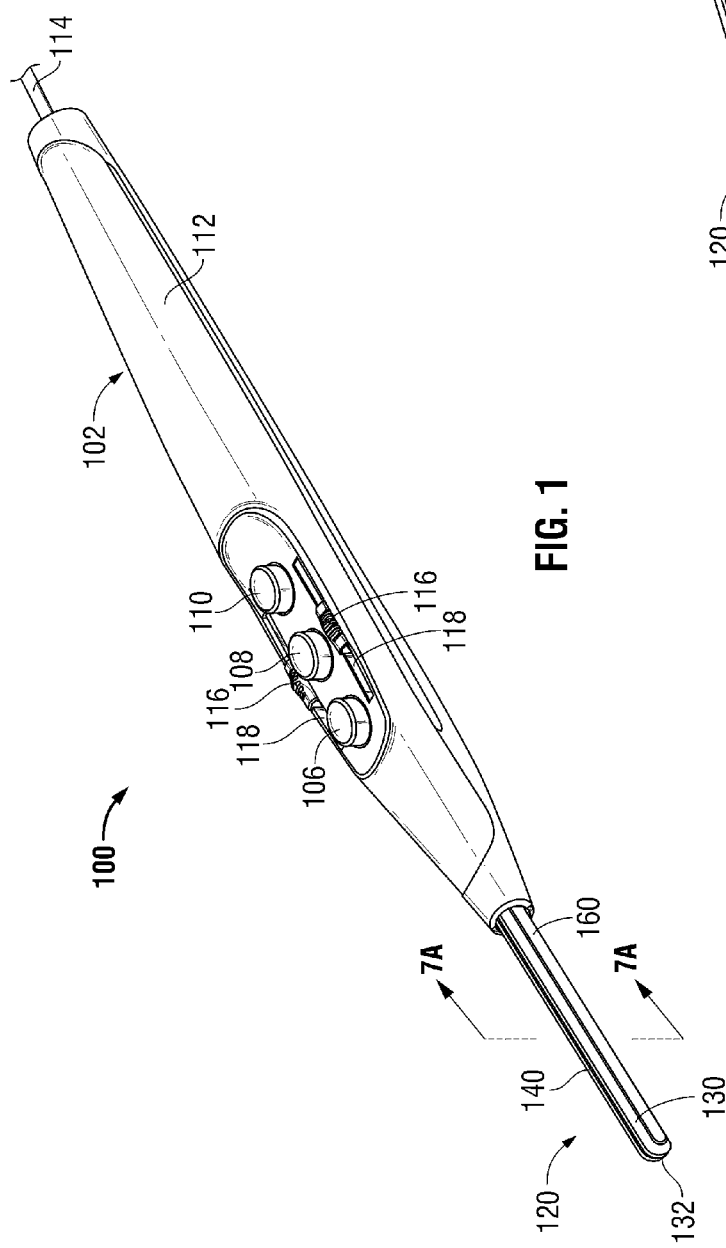
FIG. 1 is a side, perspective view of an electrosurgical pencil provided in accordance with the present disclosure.
Figure 2:
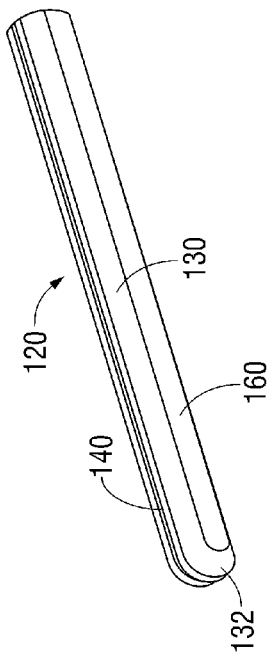
FIG. 2 is an enlarged, perspective view of an end effector of the electrosurgical pencil of FIG. 1.
Figure 7A:
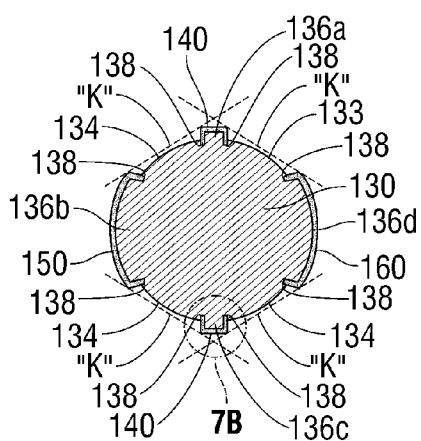
FIG. 7A is a transverse, cross-sectional view taken along section line 7A-7A of FIG. 1.

Referring to FIGS. 1-2 and 7A, electrosurgical pencil 100 includes an elongated housing 102 having an end effector 120 supported therein and extending distally therefrom. End effector 120, as will be described below, includes an electrically-insulative body, or substrate 130 having one or more electrodes 140, 150, 160 disposed thereon for electrically treating tissue in either a monopolar or bipolar mode. Electrosurgical pencil 100 may be coupled to an electrosurgical generator (not shown) or other suitable energy source via a cable 104 or, alternatively, may be configured as a battery-powered device incorporating portable power and energy generating components (not shown) within elongated housing 102. More specifically, transmission wire(s) (not shown) electrically interconnect the energy source (not shown) with the electrode(s) 140, 150, 160 disposed on end effector 120 at the proximal end of end effector 120, which extends into elongated housing 102. Similarly, control wires (not shown) electrically interconnect activation switches 106, 108, 110 supported on outer surface 112 of housing 102 with the energy source (not shown).

With continued reference to FIGS. 1-2 and 7A, activation switches 106, 108, 110 control the transmission of electrical energy to end effector 120 and/or the mode of operation of electrosurgical pencil 100. For example, one or more of activation switches 106, 108, 110 may be selectively actuated to one or more depressed positions such that a particular duty cycle and/or waveform shape is transmitted to one or more of electrodes 140, 150, 160 of end effector 120 for operation in a particular mode, e.g., a cutting and/or dissecting mode, a hemostasis mode, a combination dissecting and hemostasis mode, or any other suitable mode for electrically treating tissue as desired. Alternatively or additionally, one or more of activation switches 106, 108, 110 may be actuated to switch between a monopolar mode of operation and a bipolar mode of operation, and/or to selectively activate one or more of electrodes 140, 150, 160 of end effector 120, as desired, to electrically treat tissue.

Electrosurgical pencil 100 further includes an intensity controller 114 slidingly supported on housing 102. Intensity controller 114 includes a pair of nubs 116 which are each slidingly supported in a guide channel 118 formed in outer surface 112 of housing 102 on either side of activation switches 106, 108, 110, although other configurations are also contemplated. Intensity controller 114 may include a slide potentiometer (or other suitable intensity-control mechanism) having one or more positions, e.g., a first position corresponding to a relative low intensity setting, a second position corresponding to a relative high intensity setting, and a plurality of intermediate positions corresponding to intermediate intensity settings. Intensity controller 114 is configured to adjust the power parameters (e.g., voltage, power and/or current intensity) and/or the power verses impedance curve shape to affect the perceived output intensity.

Referring still to FIGS. 1-2 and 7A, end effector 120 of electrosurgical pencil 100 defines a generally elongated substrate 130 formed wholly from an electrically-insulative material, having an electrically-insulative coating or jacket, or otherwise having an electrically-insulative material disposed about the outer periphery thereof. Elongated substrate 130 defines a generally-cylindrical configuration having a rounded distal end 132, although other configurations are also contemplated, and includes one or more electrodes 140, 150, 160 disposed thereon that are selectively energizable for treating tissue in various different modes of operation. More specifically, elongated substrate 130 includes: a first electrode 140 extending along the generally upwardly-facing surface of substrate 130, about curved distal end 132, and along the generally downward-facing surface of substrate 130 (although the upper and lower portions of first electrode 140 may alternatively be configured as separate, independent electrodes); a second electrode 150 disposed on and extending longitudinally along one of the generally-laterally facing surfaces of substrate 130; and a third electrode 160 disposed on and extending longitudinally along the other generally-laterally facing surface of substrate 130. Electrodes 140, 150, 160 are disposed on substrate 130 in spaced-relation relative to one another whereby substrate 130 electrically insulates electrodes 140, 150, 160 from one another. Wires (not shown) electrically couple each of electrodes 140, 150, 160 to the source of energy (not shown) at the proximal end of end effector 120, which extends into housing 102, such that the electrical connections (not shown) are not exposed. Although one configuration of end effector 120 is shown, it is envisioned that greater or fewer electrodes and/or other configurations of electrodes 140, 150, 160 or of substrate 130 may be provided, depending on a particular purpose.

In use, in a bipolar mode of operation, for example, first electrode 140 may be energized to a first electrical potential, e.g., first electrode 140 may be designated as the positive, or active electrode, while second and third electrodes 150, 160, respectively, are energized to a second electrical potential, e.g., second and third electrodes 150, 160, respectively, are designated as the negative, or return electrodes, or vice versa. Electrodes 140, 150, 160 may be energized upon actuation of one or more of activation switches 106, 108, 110. Once energized, end effector 120 may be advanced into contact with tissue and/or may be advanced through tissue to electrically cut tissue, effect hemostasis, and/or otherwise electrically treat tissue. As can be appreciated, end effector 120 can be operated in various other modes of operation via selective actuation of one or more of activation switches 106, 108, 110 and/or intensity controller 114. Further, depending on the particular mode of operation, one or more of electrodes 140, 150, 160 may be selectively energized to the same potential, different potentials, or may not be energized.

Figure 3:
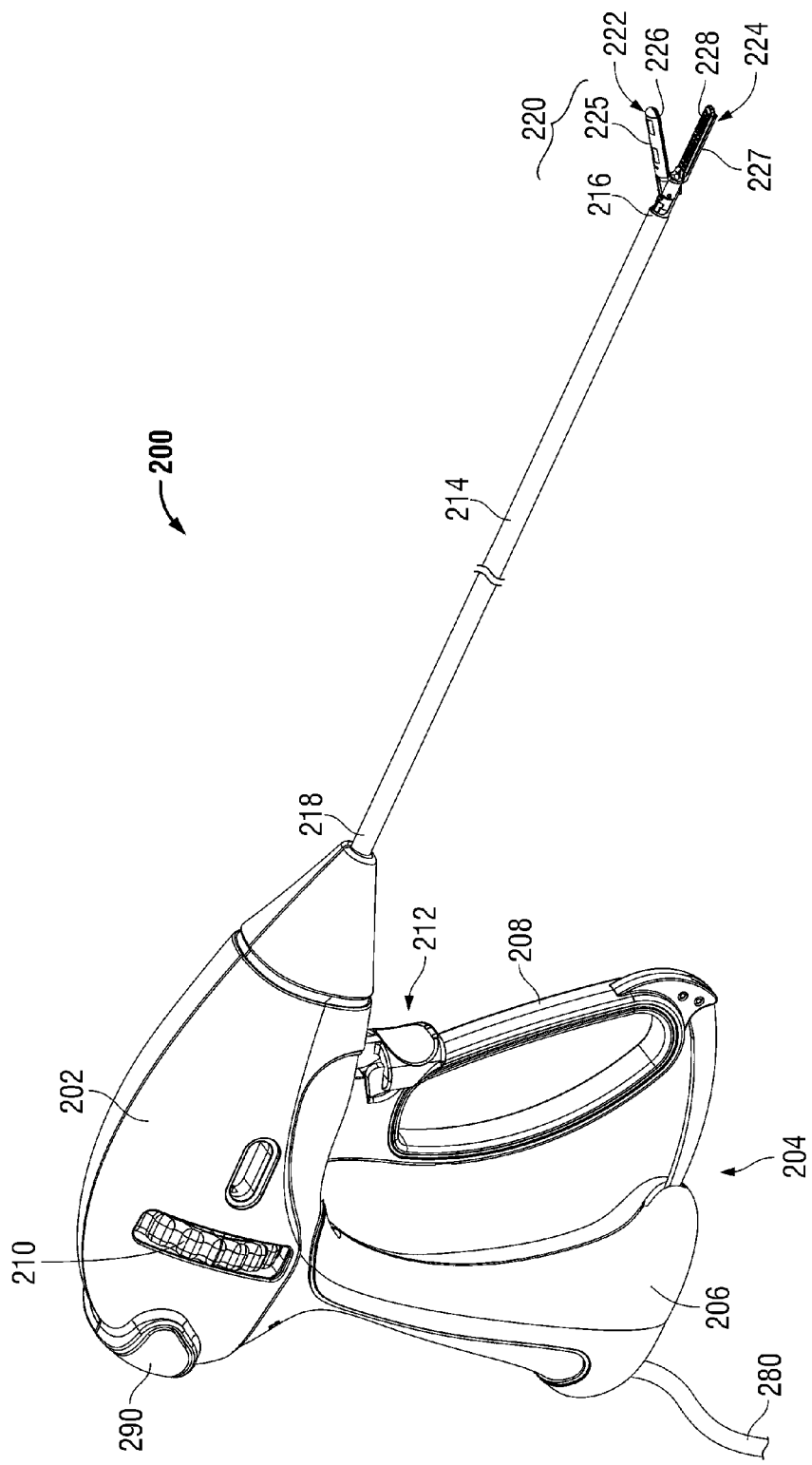
FIG. 3 is a side, perspective view of an electrosurgical forceps provided in accordance with the present disclosure.
Figure 4:
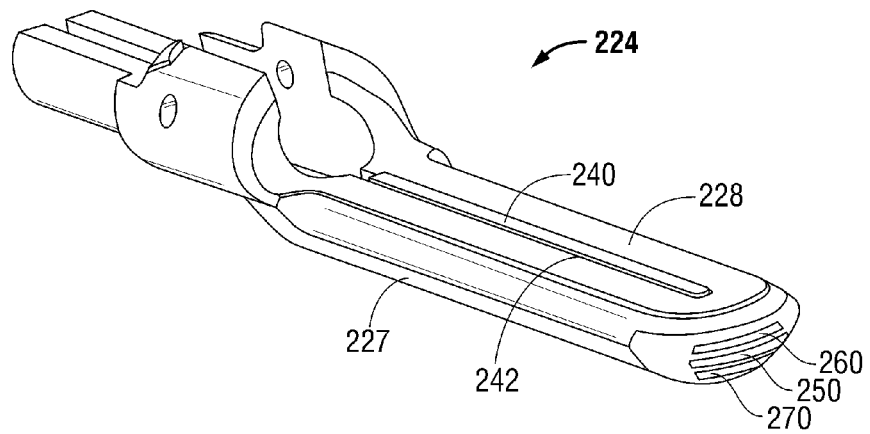
FIG. 4 is an enlarged, perspective view of a jaw member of an end effector of the electrosurgical forceps of FIG. 3.

Turning now to FIGS. 3-4, an electrosurgical forceps 200 is shown generally including a housing 202, a handle assembly 204, a rotating assembly 210, a trigger assembly 212, and an end effector 220. Forceps 200 further includes a shaft 214 having a distal end 216 configured to mechanically engage end effector 220 and a proximal end 218 that mechanically engages housing 202. Forceps 200 also includes a cable 280 that connects forceps 200 to a generator (not shown) or other suitable energy source, although forceps 200 may alternatively be configured as a battery powered instrument. Cable 280 includes wires (not shown) extending therethrough that has sufficient length to extend through shaft 214 in order to provide electrical energy to electrodes 226, 228, 240, 250, 260, 270 of end effector 220, e.g., upon selective activation of activation switch 290.

Handle assembly 204 includes a fixed handle 206 and a moveable handle 208. Fixed handle 206 is integrally associated with housing 202 and movable handle 208 is moveable relative to fixed handle 206. Rotating assembly 210 is rotatable in either direction to rotate end effector 220 about a longitudinal axis thereof. Housing 202 houses the internal working components of forceps 200.

Continuing with reference to FIGS. 3-4, end effector 220 is shown attached at distal end 216 of shaft 214 and includes a pair of opposing jaw members 222, 224. Moveable handle 208 of handle assembly 204 is ultimately connected to a drive assembly (not shown) that, together, mechanically cooperate to impart movement of jaw members 222, 224 between a spaced-apart position and an approximated position to grasp tissue disposed between electrode plates 226, 228 of jaw members 222, 224, respectively. As shown in FIG. 3, moveable handle 208 is initially spaced-apart from fixed handle 206 and, correspondingly, jaw members 222, 224 are in the spaced-apart position. Moveable handle 208 is movable from this initial position to a depressed position to move jaw members 222, 224 to the approximated position for grasping tissue therebetween. End effector 220 is designed as a unilateral assembly, e.g., where jaw member 224 is fixed relative to shaft 214 and jaw member 222 is moveable relative to shaft 214 and fixed jaw member 224 (although the reverse configuration is also contemplated). However, end effector 220 may alternatively be configured as a bilateral assembly, i.e., where both jaw member 222 and jaw member 224 are moveable relative to one another and to shaft 214.

With continued reference to FIGS. 3-4, each jaw member 222, 224, respectively, includes an insulative jaw substrate 225, 227, e.g., each jaw members 222, 225 is wholly formed from an electrically-insulative material, has an electrically-insulative coating or jacket disposed about a frame (not shown) thereof, or otherwise includes an electrically-insulative material disposed about the outer periphery thereof, and an electrode plate 226, 228 disposed atop, e.g., deposited onto, respective insulative jaw substrate 225, 227 in opposed relation relative to one another. Electrode plates 226, 228 are adapted to connect to the energy source (not shown) for conducting energy therebetween and though tissue grasped therebetween to electrically treat, e.g., seal, tissue. One or both of the jaw members, e.g., jaw member 224, may further include one or more interior electrodes, e.g., interior electrode 240, disposed on an opposed surface of insulative jaw substrate 227 of jaw member 224 between jaw members 222, 224. More specifically, interior electrode 240 is disposed within a slot 242 defined within insulative jaw substrate 227 and electrode plate 228 of jaw member 224. Interior electrode 240 is electrically insulated from electrode plate 228, e.g., via an insulator substrate (not explicitly shown) disposed within slot 242 and is adapted to connect to the energy source (not shown) for selectively energizing interior electrode 240 to electrically treat, e.g., electrically cut, tissue grasped between jaw members 222, 224. When energized, interior electrode 240 may be energized to a first potential, functioning as the active electrode, while either or both of electrode plates 226, 228 may be energized to a second, different potential, functioning as return electrodes. Monopolar operation is also contemplated.

Additionally or alternatively, one or more exterior electrodes, e.g., first, second, and third exterior electrodes 250, 260, 270, respectively, may be disposed on an outwardly-facing surface of insulative jaw substrate 227 of jaw member 224. Exterior electrodes 250, 260, 270 are likewise adapted to connect to the energy source (not shown) for conducting energy through tissue to electrically treat, e.g., dissect, tissue. Exterior electrodes 250, 260, 270 are disposed on insulative jaw substrate 227 of jaw member 224 and are electrically insulated from one another as well as from electrode plates 226, 228 and interior electrode 240. Exterior electrodes 250, 260, 270 may be configured for operation in a bipolar mode, e.g., wherein first electrode 250 is energized to a first potential and second and third electrodes 260, 270, respectively, are energized to a second potential. Alternatively, in embodiments where only a single exterior electrode is provided, the external electrode may be configured to operate in a monopolar mode (or in a bipolar mode wherein electrodes plates 226, 228 and/or interior electrode 240 function as the return electrode). In either configuration, insulative jaw substrate 227 may function as the substrate for receiving electrodes 226, 228, 240, 250, 260, and/or 270 thereon, e.g., for deposition of electrodes 226, 228, 240, 250, 260, and/or 270 thereon, or an electrically-insulative material may be disposed on the jaw frame (not explicitly shown) of either or both of jaw members 222, 224, e.g., via deposition, for receiving electrodes 226, 228, 240, 250, 260, and/or 270 thereon.

Although two exemplary embodiments, e.g., an electrosurgical pencil 100 (FIGS. 1-2) and an electrosurgical forceps 200 (FIG. 3) are described above, the present disclosure, as mentioned above, is equally applicable to any other suitable surgical instrument having an end effector including one or more electrodes for electrically treat tissue. With this in mind, manufacturing methods for forming such end effectors are described in detail below.

Turning now to FIGS. 5A-7B, manufacturing methods provided in accordance with the present disclosure for forming electrodes 140, 150, 160 on substrate 130 of end effector 120 of electrosurgical pencil 100 are described. Although described with respect to end effector 120 of electrosurgical pencil 100, the manufacturing methods described herein are equally applicable for forming any suitable surgical instrument end effector, or portion thereof, having one or more electrodes for conducting energy to tissue to electrically treat tissue, e.g., the methods described below may similarly be used in the manufacture of jaw member 222 (and/or jaw member 224) of end effector 220 of forceps 200 (see FIGS. 3-4), or any other suitable end effector of a surgical instrument.

Figure 5A:
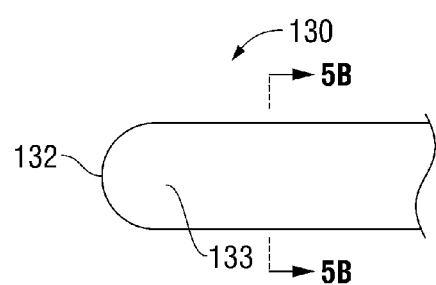
FIG. 5A is a side view of a blank substrate used in forming the end effector of the electrosurgical pencil of FIG. 1.
Figure 5B:
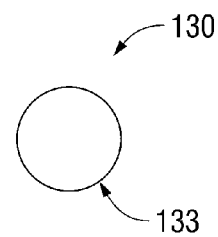
FIG. 5B is a transverse, cross-sectional view taken along section line 5B-5B of FIG. 5A.

Initially, as shown in FIGS. 5A-5B, the insulative substrate 130 is provided. Substrate 130, as mentioned above, is formed at least partially from an electrically-insulative material. More specifically, substrate 130, may be wholly formed from an electrically-insulative material, e.g., ceramic, a biopolymer, or other suitable material, may include an insulative coating or jacket disposed about a frame, e.g., a stainless steel frame, or may otherwise include an insulative portion configured to receive the electrodes thereon. Substrate 130, including the insulative portion thereof, may be formed form any suitable process, e.g., injection-molding, machining, over-molding, mechanical engagement, etc. As shown in FIGS. 5A-5B, the blank substrate 130 defines a generally cylindrical-shaped configuration having a rounded distal end 132, although other configurations are contemplated, depending on the particular requirements of the surgical instrument being manufactured and/or the particular procedure to be performed.

Figure 6A:
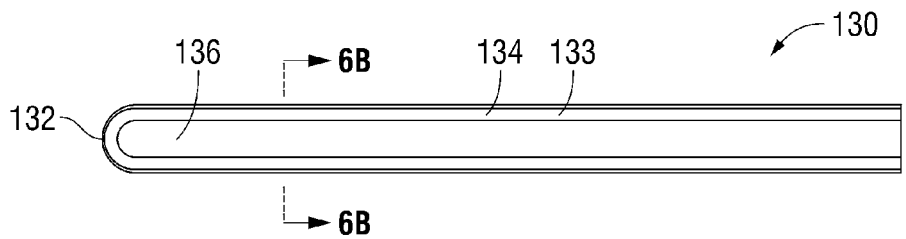
FIG. 6A is a side view of the substrate of FIG. 5A including ridges formed on the outer periphery thereof.
Figure 6B:
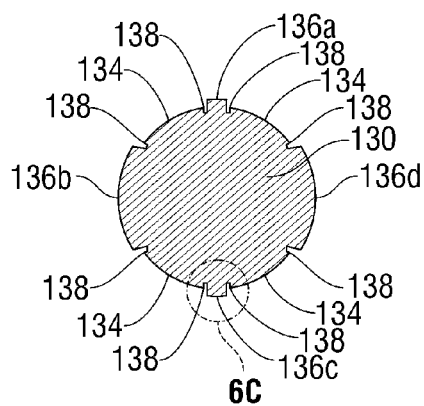
FIG. 6B is a transverse, cross-sectional view taken along section line 6B-6B of FIG. 6A.
Figure 6C:
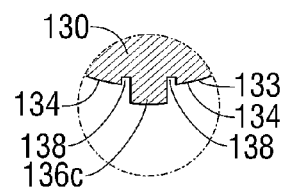
FIG. 6C is an enlarged view of the area of detail indicated in FIG. 6B.

Referring to FIGS. 6A-6C, once the blank substrate 130 is formed, or during formation of the blank substrate 132, a plurality of longitudinally-extending or otherwise configured cut-outs 134 are defined within the outer peripheral surface 133 of the blank substrate 130, e.g., via machining or other suitable process. Defining cut-outs 134 within substrate 130 forms a plurality of longitudinally-extending ridges 136 (or otherwise configured ridges, depending on the configuration of cut-outs 134) disposed about the outer periphery of substrate 130. Further, longitudinally-extending (or otherwise configured) reservoirs 138 may be formed adjacent each side of ridges 136. That is, a pair reservoirs 138 flanks each ridge 136 (one on either side thereof) and likewise flanks each cut-out 134. As will be described below, ridges 136 are configured to receive deposited electrically-conductive material thereon for forming electrodes 140, 150, 160. Thus, cut-outs 134 are defined within substrate 130 to form a particular configuration of ridges 136 in accordance with the desired configuration of electrodes 140, 150, 160 deposited on substrate 130. That is, although a particular number and configuration of cut-outs 134 and corresponding ridges 136 are defined within the outer periphery of substrate 130 in accordance with the desired configuration of the electrodes 140, 150, 160, cut-outs 134 may be defined within substrate 130 in any suitable number and/or configuration so as to define any configuration of ridges 136 in accordance with the desired configuration of electrodes 140, 150, 160 to be disposed on substrate 130.

Although substrate 130 is shown including ridges 136 (and reservoirs 138) defining generally squared-off configurations, other suitable sizes, shapes, and/or configurations are also contemplated. However, regardless of the configuration of ridges 136, it is envisioned that ridges 136 are formed such that a direct line-of-sight "K" (FIG. 7A) is established between the electrodes formed about adjacent ridges 136. Such a feature is particularly relevant when dealing with curved or other non-planar substrate surfaces, e.g., the surface of generally cylindrically-shaped substrate 130. The exact configuration, e.g., height, shape, etc., of ridges 136 necessary to establish these line-of-sights "K" depends on the shape of the substrate surface, the distance between the ridges, the thickness of the electrode to be deposited thereon, and other factors.

Figure 7B:
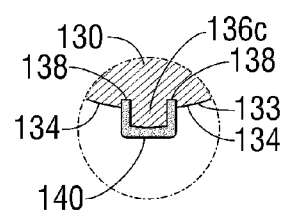
FIG. 7B is an enlarged view of the area of detail indicated in FIG. 7A.

Referring now to FIGS. 7A-7B, once cut-outs 134 and reservoirs 138 have been defined within substrate 130 to form ridges 136a, 136b, 136c, 136d (collectively ridges 136), the electrically-conductive material is disposed on each ridge 136a, 136b, 136c, 136d to form electrodes 140, 150, 160. That is, first electrode 140, which extends along both the upper and lower-facing surfaces of substrate 130 and about rounded distal end 132 (see FIG. 6A) thereof, is formed via depositing electrically-conductive material onto ridges 136a and 136c, while second and third electrodes 150, 160, respectively, are formed via depositing electrically-conductive material onto ridges 136b and 136d, respectively. The electrically-conductive material may include silver ink, gold ink, or other suitable material and may be deposited onto ridges 136 via direct-write deposition, physical vapor deposition, chemical vapor deposition, or any other suitable deposition process. Upon deposition of the electrically-conductive material onto ridges 136, rather than producing irregular edges, as may result when depositing on a smooth surface, ridges 136 allow at least some of the material to overflow ridges 136 such that at least some of the material extends over the sides of ridges 136 and, in embodiments where provided, is collected by reservoirs 138. As a result of this configuration, the electrodes 140, 150, 160 define smooth and consistent edges extending along the edges of ridges 136, with any excess material overflowing ridges 136 and extending down the side walls of ridges 136 into reservoirs 138, as shown in FIGS. 7A-7B.

One particular direct-write deposition technique that may be employed for depositing the electrically-conductive material onto ridges 136 is MICROPEN® Technologies' MICROPENNING®. MICROPENNING® is a micro-capillary technology that uses a positive displacement method of pumping flowable materials, typically having a viscosity of between about 5 and about 500,000 centipoise, onto a surface. MICROPENNING® may be used to control the volume of flowable material (e.g., electrically-conductive ink) applied, thus providing the capability to deposit one or more smooth, consistent layers of material onto ridges 136.

However, despite, the precision of MICROPENNING®, the formation of irregular edges may still occur and, thus, it is the use of MICROPENNING® in conjunction with ridges 136 (and reservoirs 138) that permits the formation of electrodes that having smooth, consistent surfaces without irregular edges.

As mentioned above, ridges 136 are formed on substrate 130 such that, upon deposition of electrodes 140, 150, 160 onto ridges 136, a direct line-of-sight "K" is established between adjacent electrodes, e.g., the upper portion of electrode 140 and electrodes 150, 160 on either side thereof, and the lower portion of electrode 140 and electrodes 150, 160 on either side thereof. As can be appreciated, the increased elevation of ridges 136 relative to outer peripheral surface 133 of substrate 130 allows for these direct line-of-sights "K," rather than having electrodes 140, 150, 160 hidden from one via substrate 130, e.g., over the horizon of the cylindrically-shaped substrate 130. It has been found that providing a direct line-of-sight "K" between adjacent electrodes adapted to conduct energy therebetween, e.g., from positive electrode 140 to negative electrodes 150, 160, facilitates the treatment of tissue at least by helping to ensure that both the positive and negative electrodes sufficiently contact tissue.

Referring to FIGS. 1-2 and 7A-7B, with the electrodes 140, 150, 160 formed on substrate 130, the proximal end of end effector 120 (FIG. 1) may be engaged within housing 102, the proximal ends of electrodes 140, 150, 160 may be coupled to the energy source (not shown), e.g., via wires and suitable electrical connections (not shown), and electrosurgical pencil 100 may be otherwise assembled to complete the manufacture thereof.

As can be appreciated, although described with respect to end effector 120, the above-described manufacturing process may be used for the manufacture of any suitable surgical instrument wherein electrodes are disposed on a substrate. That is, the above-describe methods generally remain the same regardless of the specific configuration of the surgical instrument, namely: the substrate is provided; cut-outs and, if desired, reservoirs are defined within the outer periphery of the substrate to define ridges thereon corresponding to the desired positions of the electrodes; and an electrically-conductive material is deposited onto the ridges to form the electrodes while reducing the occurrence of irregular edges, thus reducing the likelihood of arcing upon application of energy to the electrodes to treat tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing an end effector for a surgical instrument, comprising:
   providing a substrate including a first ridge defining first and second ridge edges and a ridge surface extending between the first and second ridge edges, the ridge surface being raised relative to a base surface of the substrate; and
   depositing an electrically-conductive ink onto the ridge surface via direct-write deposition such that the electrically-conductive ink covers the ridge surface and overflows the first and second ridge edges to form an electrode having an electrode surface conforming to the ridge surface and first and second electrode edges conforming to the respective first and second ridge edges.

2. The method according to claim 1, wherein providing the substrate including the first ridge includes removing portions of the substrate to define first and second cut-outs, the first ridge being defined between the first and second cut-outs.

3. The method according to claim 1, wherein the substrate further includes a reservoir defined within the base surface thereof adjacent each side of the first ridge, and wherein the electrically-conductive ink overflows the first and second ridge edges into the reservoirs.

4. The method according to claim 1, wherein the outer periphery of the substrate is formed from an electrically-insulative material.

5. The method according to claim 4, wherein the substrate is wholly formed from an electrically-insulative material or includes an electrically-insulative coating defining the outer periphery thereof.

6. The method according to claim 1, wherein the substrate further includes a second ridge defining first and second ridge edges and a ridge surface extending between the first and second ridge edges, the ridge surface of the second ridge being raised relative to the base surface of the substrate, and wherein the method further includes:
   depositing an electrically-conductive ink onto the ridge surface of the second ridge via direct-write deposition such that the electrically-conductive ink covers the ridge surface of the second ridge and overflows the first and second ridge edges of the second ridge to form a second electrode having an electrode surface conforming to the ridge surface of the second ridge and first and second electrode edges conforming to the respective first and second ridge edges of the second ridge.

7. The method according to claim 6, wherein the substrate is formed such that a direct line-of-sight is established between the ridge surfaces of the first and second ridges.

8. The method according to claim 6, further including coupling the first electrode to a positive terminal and coupling the second electrode to a negative terminal.

9. A method of manufacturing an end effector for a surgical instrument, comprising:
   providing a substrate defining an arcuate base surface and including first and second spaced-apart ridges disposed on the arcuate base surface, each of the first and second ridges defining first and second ridge edges and a ridge surface extending between the first and second ridge edges, the ridge surfaces of the first and second ridges being raised relative to the arcuate base surface;
   depositing an electrically-conductive material onto the ridge surface of the first ridge such that the electrically-conductive material covers the ridge surface and the first and second ridge edges of the first ridge to form a first electrode having an electrode surface conforming to the ridge surface of the first ridge and first and second electrode edges conforming to the respective first and second ridge edges of the first ridge; and
   depositing an electrically-conductive material onto the ridge surface of the second ridge such that the electrically-conductive material covers the ridge surface and the first and second ridge edges of the second ridge to form a second electrode having an electrode surface conforming to the ridge surface of the second ridge and first and second electrode edges conforming to the respective first and second ridge edges of the second ridge, wherein a direct line-of-sight is established between the first and second electrodes.

10. The method according to claim 9, wherein the direct-line-of-sight is established between the first or second electrode edge of the first electrode and the first or second electrode edge of the second electrode.

11. The method according to claim 9, wherein depositing electrically-conductive material onto the ridge surface of the first ridge and depositing electrically-conductive material onto the ridge surface of the second ridge are performed via direct-write deposition.

12. The method according to claim 11, wherein the electrically-conductive material is an electrically-conductive ink.

13. The method according to claim 9, further including coupling the first electrode to a positive terminal and coupling the second electrode to a negative terminal.

14. The method according to claim 9, wherein providing the substrate including the first and second spaced-apart ridges includes removing a portion of the substrate to define a cut-out between the first and second ridges.

15. The method according to claim 9, wherein the base surface of the substrate is formed from an electrically-insulative material.

16. The method according to claim 15, wherein the substrate is wholly formed from an electrically-insulative material or includes an electrically-insulative coating.

* * * * *